(12) United States Patent
Miesel

(10) Patent No.: US 7,313,440 B2
(45) Date of Patent: Dec. 25, 2007

(54) COLLECTING POSTURE AND ACTIVITY INFORMATION TO EVALUATE THERAPY

(75) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 475 days.

(21) Appl. No.: 11/106,051

(22) Filed: Apr. 14, 2005

(65) Prior Publication Data

US 2005/0245988 A1 Nov. 3, 2005

Related U.S. Application Data

(60) Provisional application No. 60/562,024, filed on Apr. 14, 2004.

(51) Int. Cl.
*A61N 1/36* (2006.01)
(52) U.S. Cl. .............................. 607/19; 607/2; 607/27; 607/62
(58) Field of Classification Search .................... 607/2, 607/3, 6, 9, 18, 19, 27, 62
See application file for complete search history.

(56) References Cited

U.S. PATENT DOCUMENTS

| | | | |
|---|---|---|---|
| 4,297,685 A | 10/1981 | Brainard, II | |
| 4,543,955 A | 10/1985 | Schroeppel | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |

(Continued)

FOREIGN PATENT DOCUMENTS

DE 198 31 109 1/2000

(Continued)

OTHER PUBLICATIONS

M.T. Smith et al., "Presleep Cognitions in Patients with Insomnia Secondary to Chronic Pain," Journal of Behavioral Medicine, vol. 24, No. 1, pp. 93-114, 2001.

(Continued)

*Primary Examiner*—Kennedy J. Schaetzle
(74) *Attorney, Agent, or Firm*—John W. Albrecht; Medtronic, Inc.

(57) ABSTRACT

A medical device, programmer, or other computing device may determine values of one or more activity and, in some embodiments, posture metrics for each therapy parameter set used by the medical device to deliver therapy. The metric values for a parameter set are determined based on signals generated by the sensors when that therapy parameter set was in use. Activity metric values may be associated with a postural category in addition to a therapy parameter set, and may indicate the duration and intensity of activity within one or more postural categories resulting from delivery of therapy according to a therapy parameter set. A posture metric for a therapy parameter set may indicate the fraction of time spent by the patient in various postures when the medical device used a therapy parameter set. The metric values may be used to evaluate the efficacy of the therapy parameter sets.

29 Claims, 10 Drawing Sheets

U.S. PATENT DOCUMENTS

| | | |
|---|---|---|
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,832,932 A | 11/1998 | Elsberry et al. |
| 5,895,371 A | 4/1999 | Levitas et al. |
| 5,904,708 A | 5/1999 | Goedeke |
| 5,904,780 A | 5/1999 | Tomoyasu |
| 5,919,149 A | 7/1999 | Allum |
| 5,941,906 A | 8/1999 | Barreras, Sr. et al. |
| 5,944,680 A | 8/1999 | Christopherson et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,351,672 B1 | 2/2002 | Park et al. |
| 6,366,813 B1 | 4/2002 | DiLorenzo |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,130,689 B1 * | 10/2006 | Turcott ......................... 607/27 |
| 7,162,304 B1 | 1/2007 | Bradley |
| 7,209,787 B2 | 4/2007 | DiLorenzo |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2005/0021103 A1 | 1/2005 | DiLorenzo |
| 2005/0021104 A1 | 1/2005 | DiLorenzo |
| 2005/0042589 A1 | 2/2005 | Hatlestad et al. |
| 2005/0113710 A1 | 5/2005 | Stahmann et al. |
| 2005/0119703 A1 | 6/2005 | DiLorenzo |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0293720 A1 | 12/2006 | DiLorenzo |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| DE | 100 24 103 | 11/2001 |
| EP | 0 564 803 | 10/1993 |
| EP | 0 849 715 B1 | 6/1998 |
| EP | 1 195 139 | 4/2002 |
| EP | 1 195 139 A1 | 4/2002 |
| EP | 1 291 036 | 3/2003 |
| EP | 1 308 182 | 5/2003 |
| EP | 1 308 182 A2 | 5/2003 |
| EP | 1 437 159 | 7/2004 |
| EP | 1 437 159 A1 | 7/2004 |
| EP | 1 322 227 B1 | 12/2005 |
| GB | 2 330 912 | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |

WO WO 2005/035050 4/2005

OTHER PUBLICATIONS

M.T. Smith et al., "How do sleep disturbance and chronic pain inter-relate? Insights from the longitudinal and cognitive-behavioral clinical trials literature," Sleep Medicine Reviews, YSMRV 286, pp. 1-14, Jun. 19, 2003.

Suanne Goodrich et al., "The Predicition of Pain Using Measures of Sleep Quality," Pain Digest (1998) 8:23-25.

"Analysis of heart rate dynamics by methods derived from nonlinear mathematics: Clinical applicability and prognostic significance" http:/herkules.oulu.fi.isbn9514250133/html/x222.html, 4 pgs. (downloaded 2004).

International Search Report and Written Opinion for corresponding PCT Appl. No. PCT/US2005/012838, mailed Aug. 1, 2005 (11 pgs).

"Watch," Wikipedia, the free encyclopedia, 6 pgs., http://en.wikipedia.org/wiki/Watch, (2006).

"IBM & Citizen Watch develop Linuz-based 'WatchPad'," 5 pgs., http://www.linuxdevices.com/news/NS6580187845.html, (2006).

Tuisku, Katinka, "Motor Activity Measured By Actometry in Neuropsychiatric Disorders," Department of Psychiatry, University of Helsinski, Helsinki, Finland, 115 pgs., (2002).

Kassam, M., "2005 EDP Topic 'MK4': Tremor Data-Logger for Parkinson's Disease Patients," http://www.ee.ryerson.ca/~courses/edp2005/MK4.html, 3 pgs., (2006).

"Design Competition: Runners-Up for the Best Three Designs," EPN, vol. 26, No. 1, (2002).

"MiniMitter® Physiological and Behavioral Monitoring for Humans and Animals," http://www.minimitter.com/Products/Actiwatch, 3 pgs., (2006).

Notification of Transmittal of the International Preliminary Report on Patentability, dated Jul. 26, 2006, for corresponding PCT Appl. No. PCT/US2005/012838, filed Apr. 14, 2005 (11 pages).

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/cmsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG.., http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.html, 2 pgs. Jan. 31, 2005.

Sleep Strip & Bite Strip, http://www.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparsions.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

* cited by examiner

| PARAMETER SET | PARAMETERS | POSTURE | % OF TIME ACTIVE | COUNTS/HOUR |
|---|---|---|---|---|
| 1 | PA = 5.5V<br>PW = 210ms<br>PR = 90Hz | UPRIGHT (52%)<br>RECUMBENT (48%) | 75% (15% HIGH)<br>10% (2% HIGH) | 100<br>10 |
| 2 | PA = 5V<br>PW = 190ms<br>PR = 95Hz | UPRIGHT (45%)<br>RECUMBENT (55%) | 68% (4% HIGH)<br>10% (1% HIGH) | 67<br>12 |
| ••• | | | | |
| N | PA = 4.6V<br>PW = 215ms<br>PR = 80Hz | UPRIGHT (40%)<br>RECUMBENT (60%) | 62% (4% HIGH)<br>8% (1% HIGH) | 72<br>13 |

COLLECTING POSTURE AND ACTIVITY INFORMATION TO EVALUATE THERAPY

This application claims the benefit of U.S. Provisional Application Ser. No. 60/562,024, filed Apr. 14, 2004, the entire content of which is incorporated herein by reference.

TECHNICAL FIELD

The invention relates to medical devices and, more particularly, to medical devices that deliver therapy.

BACKGROUND

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders and congestive heart failure. When a patient is inactive, he may be more likely to be recumbent, i.e., lying down, or sitting, and may change postures less frequently.

In some cases, these ailments are treated via a medical device, such as an implantable medical device (IMD). For example, patients may receive an implantable neurostimulator or drug delivery device to treat chronic pain or a movement disorder. Congestive heart failure may be treated by, for example, a cardiac pacemaker.

SUMMARY

In general, the invention is directed to techniques for evaluating a therapy delivered to a patient by a medical device based on patient activity, posture, or both. At any given time, the medical device delivers the therapy according to a current set of therapy parameters. The therapy parameters may be changed over time such that the therapy is delivered according to a plurality of different therapy parameter sets. The invention may provide techniques for evaluating the relative efficacy of the plurality of therapy parameter sets.

A system according to the invention may include a medical device that delivers therapy to a patient, one or more programmers or other computing devices that communicate with the medical device, and one or more sensors that generate signals as a function of at least one of patient activity and posture. The medical device, programmer, or other computing device may determine values of one or more activity metrics and, in some embodiments, may also determine posture metric values for each therapy parameter set used by the medical device to deliver therapy. The activity and posture metric values for a therapy parameter set are determined based on the signals generated by the sensors when that therapy parameter set was in use. The activity metric value may indicate a level of activity when the medical device used a particular therapy parameter set. Activity metric values may be associated with a postural category in addition to a therapy parameter set, and may indicate the duration and intensity of activity within one or more postural categories resulting from delivery of therapy according to a therapy parameter set. A posture metric value for a therapy parameter set may indicate the fraction of time spent by the patient in various postures when the medical device used a particular therapy parameter set.

A clinician may use the one or more activity or posture metric values to evaluate therapy parameter sets used by the medical device to deliver therapy, or a sensitivity analysis may identify one or more potentially efficacious therapy parameter sets based on the metric values. In either case, the activity and/or posture metric values may be used to evaluate the relative efficacy of the parameter sets, and the parameter sets that support the highest activity levels and most upright and active postures for the patient may be readily identified.

In one embodiment, the invention is directed to a method in which a plurality of signals are monitored. Each of the signals is generated by a sensor as a function of at least one of activity or posture of a patient. A posture of the patient is periodically identified based on at least one of the signals, and each of the identified postures is associated with a therapy parameter set currently used by a medical device to deliver a therapy to a patient when the posture is identified. An activity level of the patient is periodically determined based on at least one of the signals, and each of the determined activity levels is associated with a therapy parameter set currently used by a medical device to deliver a therapy to a patient when the activity level is identified, and with a current one of the periodically identified postures. For each of a plurality of therapy parameter sets used by the medical device to deliver therapy to the patient, a value of an activity metric may be determined for each of the periodically identified postures associated with the therapy parameter set based on the activity levels associated with the posture and the therapy parameter set.

In another embodiment, the invention is directed to medical system comprising a plurality of sensors, each of the sensors generating a signal as a function of at least one of activity or posture of a patient, a medical device that delivers a therapy to the patient, and a processor. The processor monitors the signals generated by the sensors, periodically identifies a posture of the patient based on at least one of the signals, associates each of the identified postures with a therapy parameter set currently used by a medical device to deliver a therapy to a patient when the posture is identified, periodically determines an activity level of the patient based on at least one of the signals, associates each of the determined activity levels with a therapy parameter set currently used by a medical device to deliver a therapy to a patient when the activity level is determined and a current one of the periodically identified postures, and, for each of a plurality of therapy parameter sets used by the medical device to deliver therapy to the patient, determines a value of an activity metric for each of the periodically identified postures associated with the therapy parameter set based on the activity levels associated with the posture and the therapy parameter set.

In another embodiment, the invention is directed to a computer-readable medium comprising instructions. The instructions cause a programmable processor to monitor a plurality of signals, each of the signals generated by a sensor as a function of at least one of activity or posture of a patient. The instructions further cause the processor to periodically identify a posture of the patient based on at least one of the signals, and associate each of the identified postures with a therapy parameter set currently used by a medical device to deliver a therapy to a patient when the posture is identified. The instructions further cause the processor to periodically determine an activity level of the patient based on at least one of the signals, and associate each of the determined activity levels with a therapy parameter set currently used by a medical device to deliver a therapy to a patient when the activity level is determined and a current one of the periodically identified postures. The instructions further cause the processor to, for each of a plurality of therapy parameter sets used by the medical device to deliver therapy to the patient, determine a value of an activity metric for each of the periodically identified postures associated with the therapy parameter set based on the activity levels associated with the posture and the therapy parameter set.

In another embodiment, the invention is directed to a method in which a plurality of signals are monitored, each of the signals generated by a sensor as a function of at least one of activity or posture of a patient. Whether the patient is in a target posture is determined based on at least one of the signals, and an activity level of the patient is periodically determined based on at least one of the signals when the patient is in the target posture. Each of the determined activity levels is associated with a current therapy parameter set and, for each of a plurality of therapy parameter sets used by the medical device to deliver therapy to the patient, a value of an activity metric is determined based on the activity levels associated with the therapy parameter set.

In another embodiment, the invention is directed to a medical system comprising a plurality of sensors, each of the sensors generating a signal as a function of at least one of activity or posture of a patient, a medical device that delivers a therapy to the patient, and a processor. The processor monitors the signals generated by the sensors, periodically identifies a posture of the patient based on at least one of the signals, determines whether the patient is in target posture based on at least one of the signals, periodically determines an activity level of the patient based on at least one of the signals when the patient is in the target posture, associates each of the determined activity levels with a current therapy parameter set, and for each of a plurality of therapy parameter sets used by the medical device to deliver therapy to the patient, determines a value of an activity metric based on the activity levels associated with the therapy parameter set.

In another embodiment, the invention is directed to a computer-readable medium comprising instructions. The instructions cause a programmable processor to monitor a plurality of signals, each of the signals generated by a sensor as a function of at least one of activity or posture of a patient, determine whether the patient is in target posture based on at least one of the signals, periodically determine an activity level of the patient based on at least one of the signals when the patient is in the target posture, associate each of the determined activity levels with a current therapy parameter set, and for each of a plurality of therapy parameter sets used by the medical device to deliver therapy to the patient, determine a value of an activity metric based on the activity levels associated with the therapy parameter set.

The invention is capable of providing one or more advantages. For example, a medical system according to the invention may provide a clinician with an objective indication of the efficacy of different sets of therapy parameters. The indication of efficacy may be provided in terms of the ability of the patient to assume particular postures and activity levels for each given set of therapy parameters, permitting identification of particular sets of therapy parameters that yield the highest efficacy. Further, a medical device, programming device, or other computing device according to the invention may display therapy parameter sets and associated metric values in an ordered and, in some cases, sortable list, which may allow the clinician to more easily compare the relative efficacies of a plurality of therapy parameter sets. The medical system may be particularly useful in the context of trial neurostimulation for treatment of chronic pain, where the patient is encouraged to try a plurality of therapy parameter sets to allow the patient and clinician to identify efficacious therapy parameter sets. Further, in some embodiments, the system may provide at least semi-automated identification of potentially efficacious therapy parameter sets, through application of a sensitivity analysis to one or more activity or posture metrics.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 7 illustrates an example list of therapy parameter sets and associated posture and activity metric values that may be presented by a clinician programmer.

DETAILED DESCRIPTION

Figure 1:
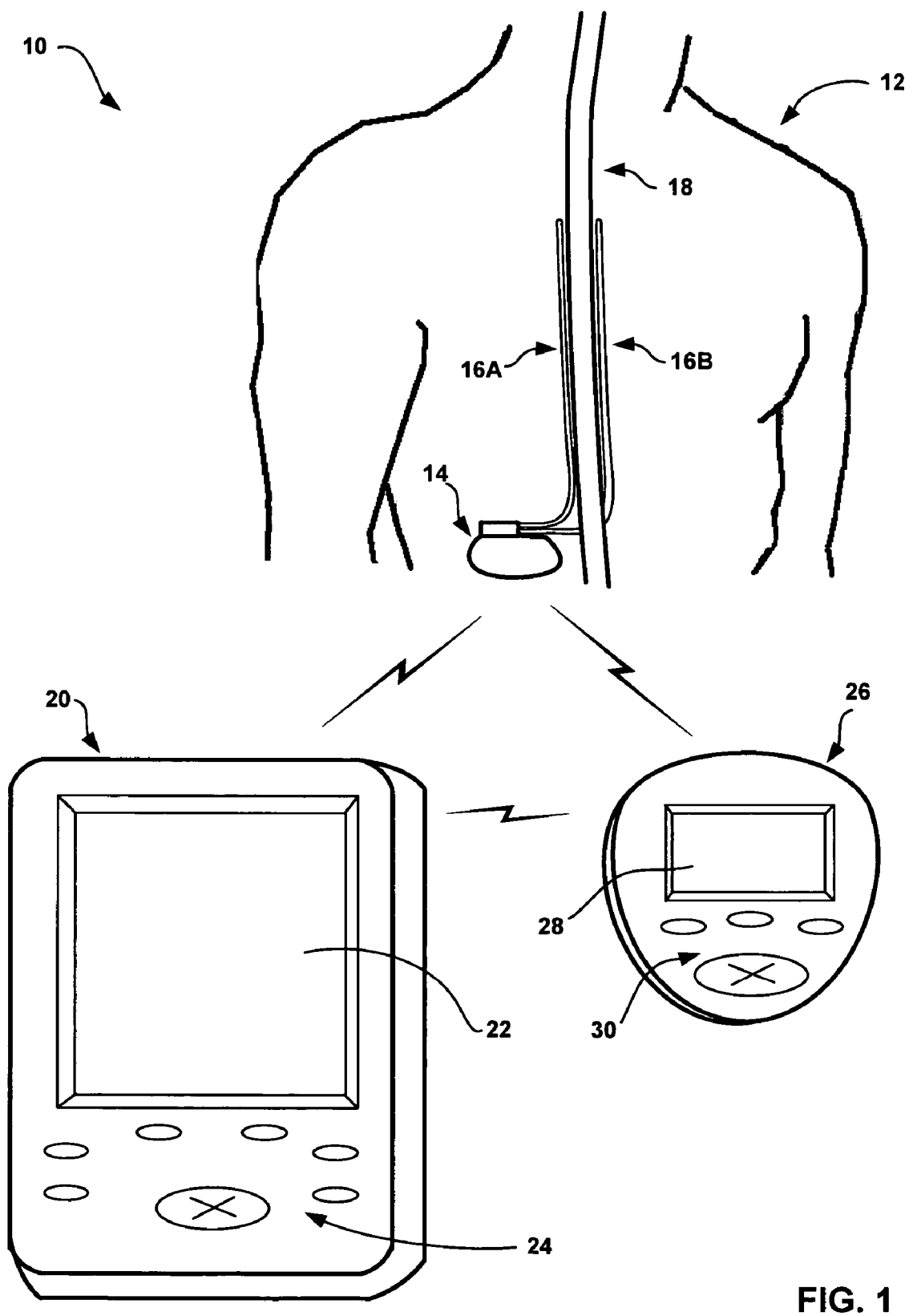
FIG. 1 is a conceptual diagram illustrating an example system that includes an implantable medical device that collects posture and activity information according to the invention.

FIG. 1 is a conceptual diagram illustrating an example system 10 that includes an implantable medical device (IMD) 14 that collects information relating to the activity and, in some embodiments, the posture of a patient 12. In the illustrated example system 10, IMD 14 takes the form of an implantable neurostimulator that delivers neurostimulation therapy in the form of electrical pulses to patient 12. However, the invention is not limited to implementation via an implantable neurostimulator. For example, in some embodiments of the invention, IMD 14 may take the form of an implantable pump or implantable cardiac rhythm management device, such as a pacemaker, that collects activity and posture information. Further, the invention is not limited to implementation via an IMD. In other words, any implantable or external medical device may collect activity and posture information according to the invention.

In the example of FIG. 1, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence, sexual dysfunction, or gastroparesis.

IMD 14 delivers therapy according to a set of therapy parameters, i.e., a set of values for a number of parameters that define the therapy delivered according to that therapy parameter set. In embodiments where IMD 14 delivers neurostimulation therapy in the form of electrical pulses, the parameters in each parameter set may include voltage or current pulse amplitudes, pulse widths, pulse rates, duration, duty cycle and the like. Further, each of leads 16 includes electrodes (not shown in FIG. 1), and a therapy parameter set may include information identifying which electrodes have been selected for delivery of pulses, and the polarities of the selected electrodes. Therapy parameter sets used by IMD 14 may include a number of parameter sets programmed by a clinician (not shown), and parameter sets representing adjustments made by patient 12 to these preprogrammed sets.

System 10 also includes a clinician programmer 20. The clinician may use clinician programmer 20 to program therapy for patient 12, e.g., specify a number of therapy parameter sets and provide the parameter sets to IMD 14. The clinician may also use clinician programmer 20 to retrieve information collected by IMD 14. The clinician may use clinician programmer 20 to communicate with IMD 14 both during initial programming of IMD 14, and for collection of information and further programming during follow-up visits.

Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus or mouse. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of therapy by IMD 14. For example, using patient programmer 26, patient 12 may select a current therapy parameter set from among the therapy parameter sets preprogrammed by the clinician, or may adjust one or more parameters of a preprogrammed therapy parameter set to arrive at the current therapy parameter set.

Patient programmer 26 may include a display 28 and a keypad 30, to allow patient 12 to interact with patient programmer 26. In some embodiments, display 26 may be a touch screen display, and patient 12 may interact with patient programmer 26 via display 28. Patient 12 may also interact with patient programmer 26 using peripheral pointing devices, such as a stylus, mouse, or the like.

Clinician and patient programmers 20, 26 are not limited to the hand-held computer embodiments illustrated in FIG. 1. Programmers 20, 26 according to the invention may be any sort of computing device. For example, a programmer 20, 26 according to the invention may be a tablet-based computing device, a desktop computing device, or a workstation.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 collects patient activity information. Specifically, as will be described in greater detail below, IMD 14 periodically determines an activity level of patient 12 based on a signal that varies as a function of patient activity. An activity level may comprise, for example, a number of activity counts, or a value for a physiological parameter that reflects patient activity.

In some embodiments, IMD 14 also collects patient posture information. In such embodiments, IMD 14 may monitor one or more signals that vary as a function of patient posture, and may identify postures based on the signals. IMD 14 may, for example, periodically identify the posture of patient 12 or transitions between postures made by patient 12. For example, IMD 14 may identify whether the patient is upright or recumbent, e.g., lying down, whether the patient is standing, sitting, or recumbent, or transitions between such postures.

In exemplary embodiments, as will be described in greater detail below, IMD 14 monitors the signals generated by a plurality of accelerometers. In such embodiments, IMD 14 may both determine activity levels and identify postures or postural transitions based on the accelerometer signals. Specifically, IMD 14 may compare the DC components of the accelerometer signals to one or more thresholds to identify postures, and may compare a non-DC portion of one or more of the signals to one or more thresholds to determine activity levels.

Over time, IMD 14 may use a plurality of different therapy parameter sets to deliver the therapy to patient 12. In some embodiments, IMD 14 associates each determined posture with the therapy parameter set that is currently active when the posture is identified. In such embodiments, IMD 14 may also associate each determined activity level with the currently identified posture, and with the therapy parameter set that is currently active when the activity level is determined. In other embodiments, IMD 14 may use posture to control whether activity levels are monitored. In such embodiments, IMD 14 determines whether patient 12 is in a target posture, e.g., a posture of interest such as upright or standing, and determines activity levels for association with current therapy parameter sets during periods when the patient is in the target posture.

In either case, IMD 14 may determine at least one value of one or more activity metrics for each of the plurality of therapy parameter sets based on the activity levels associated with the therapy parameter sets. An activity metric value may be, for example, a mean or median activity level, such as an average number of activity counts per unit time. In other embodiments, an activity metric value may be chosen from a predetermined scale of activity metric values based on a comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set.

In embodiments in which IMD 14 associates identified postures with the current therapy parameter set, and associates each determined activity level with a current posture and the current therapy parameter set, IMD 14 may, for each therapy parameter set, identify the plurality of postures assumed by patient 12 when that therapy parameter set was in use. IMD 14 may then determine a value of one or more activity metrics for each therapy parameter set/posture pair based on the activity levels associated with that therapy parameter set/posture pair.

Further, for each therapy parameter set, IMD 14 may also determine a value of one or more posture metrics based on the postures or postural transitions associated with that therapy parameter set. A posture metric value may be, for example, an amount or percentage of time spent in a posture while a therapy parameter set is active, e.g., an average amount of time over a period of time, such as an hour, that patient 12 was within a particular posture. In some embodiments, a posture metric value may be an average number of posture transitions over a period of time, e.g., an hour.

In some embodiments, a plurality of activity metric values are determined for each of the plurality of therapy parameter sets, or parameter set/posture pairs. In such embodiments, an overall activity metric value may be determined. For example, the plurality of individual activity metric values may be used as indices to identify an overall activity metric value from a look-up table. The overall activity metric may be selected from a predetermined scale of activity metric values, which may be numeric, such as activity metric values from 1-10, or qualitative, such as low, medium or high activity.

Similarly, in some embodiments, a plurality of posture metric values is determined for each of the plurality of therapy parameter sets. In such embodiments, an overall posture metric value may be determined. For example, the plurality of individual posture metric values may be used as indices to identify an overall posture metric value from a look-up table. The overall posture metric may be selected from a predetermined scale of posture metric values, which may be numeric, such as posture metric values from 1-10.

Although described herein primarily with reference to IMD 14, one or more of IMD 14, clinician programmer 20, patient programmer 26, or another computing device may determine activity and posture metric values in the manner described herein with reference to IMD 14. For example, in some embodiments, IMD 14 determines and stores metric values, and provides information identifying therapy parameter sets and the metric values associated with the therapy parameter sets, to one or both of programmers 20, 26. In other embodiments, IMD 14 provides information identifying the therapy parameter sets and associated posture events and activity levels to one or both of programmers 20, 26, or another computing device, and the programmer or other computing device determines activity and posture metric values for each of the therapy parameter sets.

In either of these embodiments, programmers 20, 26 or the other computing device may present information to a user that may be used to evaluate the therapy parameter sets based on the activity and posture metric values. For ease of description, the presentation of information that may be used to evaluate therapy parameter sets will be described hereafter with reference to embodiments in which clinician programmer 20 presents information to a clinician. However, it is understood that, in some embodiments, patient programmer 26 or another computing device may present such information to a user, such as a clinician or patient 12.

For example, in some embodiments, clinician programmer 20 may present a list of the plurality of parameter sets and associated posture and activity metric values to the clinician via display 22. Where values are determined for a plurality of posture and activity metrics for each of the therapy parameter sets, programmer 20 may order the list according to the values of one of the metrics that is selected by the clinician. Programmer 20 may also present other activity and/or posture information to the clinician, such as graphical representations of activity and/or posture. For example, programmer 20 may present a trend diagram of activity or posture over time, or a histogram or pie chart illustrating percentages of time that activity levels were within certain ranges or that patient 12 assumed certain postures. Programmer 20 may generate such charts or diagrams using activity levels or posture events associated with a particular one of the therapy parameter sets, or all of the activity levels and posture events determined by IMD 14.

However, the invention is not limited to embodiments that include programmers 20, 26 or another computing device, or embodiments in which a programmer or other computing device presents posture and activity information to a user. For example, in some embodiments, an external medical device comprises a display. In such embodiments, the external medical device both determines the metric values for the plurality of therapy parameter sets, and presents the list of therapy parameter sets and associated metric values.

Further, the invention is not limited to embodiments in which a medical device determines activity levels or identifies postures. For example, in some embodiments, IMD 14 may instead periodically record samples of one or more signals, and associate the samples with a current therapy parameter set. In such embodiments, a programmer 20, 26 or another computing device may receive information identifying a plurality of therapy parameter sets and the samples associated with the parameter sets, determine activity levels and identify postures and postural transitions based on the samples, and determine one or more activity and/or posture metric values for each of the therapy parameter sets based on the determined activity levels and identified postures.

Moreover, the invention is not limited to embodiments in which the therapy delivering medical device includes or is coupled to the sensors that generate a signal as a function of patient activity or posture. In some embodiments, system 10 may include a separate implanted or external monitor that includes or is coupled to such sensors. The monitor may provide samples of the signals generated by such sensors to the IMD, programmers or other computing device for determination of activity levels, postures, activity metric values and posture metric values as described herein.

The monitor may provide the samples in real-time, or may record samples for later transmission. In embodiments where the monitor records the samples for later transmission, the monitor may associate the samples with the time they were recorded. In such embodiments, the IMD 14 may periodically record indications of a currently used therapy parameter set and the current time. Based on the association of recorded signal samples and therapy parameter sets with time, the recorded signal samples may be associated with current therapy parameter sets for determination of activity and posture metric values as described herein.

In some embodiments, in addition to, or as an alternative to the presentation of information to a clinician for evaluation of therapy parameter sets, one or more of IMD 14, programmers 20, 26, or another computing device may identify therapy parameter sets for use in delivery of therapy to patient 12 based on a sensitivity analysis of one or more activity and/or posture metrics. The sensitivity analysis identifies values of therapy parameters that define a substantially maximum or minimum value of the one or more metrics. In particular, as will be described in greater detail below, one or more of IMD 14 and programmers 20, 26 conducts the sensitivity analysis of the one or more metrics, and identifies at least one baseline therapy parameter set that includes the values for individual therapy parameters that were identified based on the sensitivity analysis. IMD 14 may delivery therapy according to the baseline therapy parameter set. Furthermore, one or more of IMD 14 and programmers 20, 26 may periodically perturb at least one therapy parameter value of the baseline therapy parameter set to determine whether the baseline therapy parameter set still defines a substantially maximum or minimum value of the one or more metrics. If the baseline therapy parameter set no longer defines a substantially maximum or minimum value of the one or more metrics, a search may be performed to identify a new baseline therapy parameter set for use in delivery of therapy to patient 12.

Figure 2:
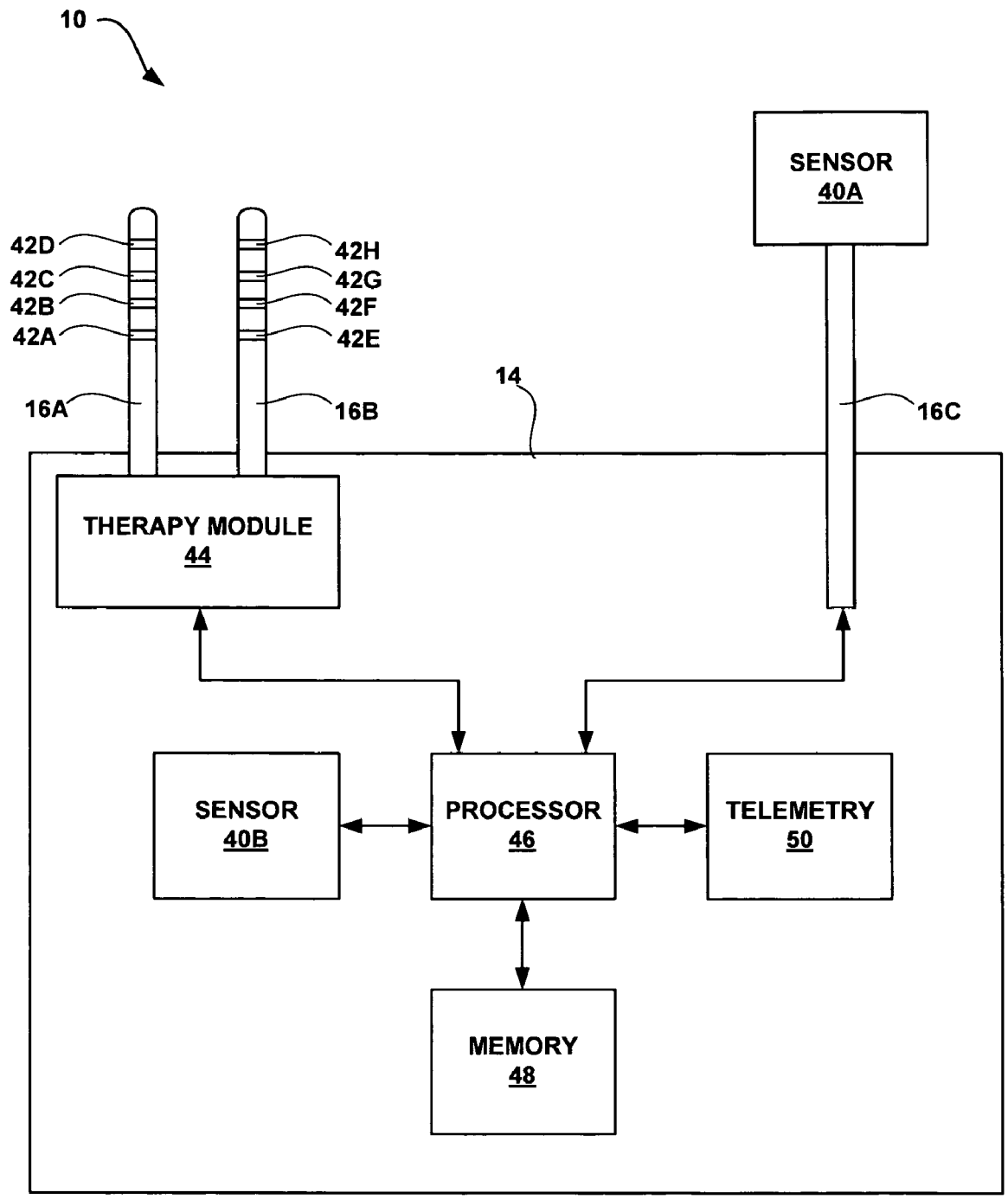
FIG. 2 is a block diagram further illustrating the example system and implantable medical device of FIG. 1.

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals that vary as a function of patient activity and/or posture. As will be described in greater detail below, IMD 14 monitors the signals, and may periodically identify the posture of patient 12 and determine an activity level based on the signals.

IMD 14 may deliver neurostimulation therapy via electrodes 42A-D of lead 16A and electrodes 42E-H of lead 16B (collectively "electrodes 40"). Electrodes 40 may be ring electrodes. The configuration, type and number of electrodes 40 illustrated in FIG. 2 are merely exemplary. For example, leads 16A and 16B may each include eight electrodes 40, and the electrodes 42 need not be arranged linearly on each of leads 16A and 16B.

Electrodes 42 are electrically coupled to a therapy delivery module 44 via leads 16A and 16B. Therapy delivery module 44 may, for example, include an output pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to a current therapy parameter set. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal that varies as a function of patient activity and/or posture. IMD 14 may include circuitry (not shown) that conditions the signals generated by sensors 40 such that they may be analyzed by processor 46. For example, IMD 14 may include one or more analog to digital converters to convert analog signals generated by sensors 40 into digital signals usable by processor 46, as well as suitable filter and amplifier circuitry. Although shown as including two sensors 40, system 10 may include any number of sensors.

Further, as illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor 40 located outside of IMD 14 may be in wireless communication with processor 46. Wireless communication between sensors 40 and IMD 14 may, as examples, include RF communication or communication via electrical signals conducted through the tissue and/or fluid of patient 12.

In exemplary embodiments, sensors 40 include a plurality of accelerometers, e.g., three accelerometers, which are oriented substantially orthogonally with respect to each other. In addition to being oriented orthogonally with respect to each other, each of accelerometers may be substantially aligned with an axis of the body of patient 12. The magnitude and polarity of DC components of the signals generated by the accelerometers indicate the orientation of the patient relative to the Earth's gravity, and processor 46 may periodically identify the posture or postural changes of patient 12 based on the magnitude and polarity of the DC components. Further information regarding use of orthogonally aligned accelerometers to determine patient posture may be found in a commonly assigned U.S. Pat. No. 5,593,431, which issued to Todd J. Sheldon.

Processor 46 may periodically determine the posture of patient 12, and may store indications of the determined postures within memory 48. Where system 10 includes a plurality of orthogonally aligned accelerometers located on or within the trunk of patient 12, e.g., within IMD 14 which is implanted within the abdomen of patient 12 as illustrated in FIG. 1, processor 46 may be able to periodically determine whether patient is, for example, upright or recumbent, e.g., lying down. In embodiments of system 10 that include an additional one or more accelerometers at other locations on or within the body of patient 12, processor 46 may be able to identify additional postures of patient 12. For example, in an embodiment of system 10 that includes one or more accelerometers located on or within the thigh of patient 12, processor 46 may be able to identify whether patient 12 is standing, sitting, or lying down. Processor 46 may also identify transitions between postures based on the signals output by the accelerometers, and may store indications of the transitions, e.g., the time of transitions, within memory 48.

Processor 46 may identify postures and posture transitions by comparing the signals generated by the accelerometers to one or more respective threshold values. For example, when patient 12 is upright, a DC component of the signal generated by one of the plurality of orthogonally aligned accelerometers may be substantially at a first value, e.g., high or one, while the DC components of the signals generated by the others of the plurality of orthogonally aligned accelerometers may be substantially at a second value, e.g., low or zero. When patient 12 becomes recumbent, the DC component of the signal generated by one of the plurality of orthogonally aligned accelerometers that had been at the second value when the patient was upright may change to the first value, and the DC components of the signals generated by others of the plurality of orthogonally aligned accelerometers may remain at or change to the second value. Processor 46 may compare the signals generated by such sensors to respective threshold values stored in memory 48 to determine whether they are substantially at the first or second value, and to identify when the signals change from the first value to the second value.

Processor 46 may determine an activity level based on one or more of the accelerometer signals by sampling the signals and determining a number of activity counts during the sample period. For example, processor 46 may compare the sample of a signal generated by an accelerometer to one or more amplitude thresholds stored within memory 48, and may identify each threshold crossing as an activity count. Where processor 46 compares the sample to multiple thresholds with varying amplitudes, processor 46 may identify crossing of higher amplitude thresholds as multiple activity counts. Using multiple thresholds to identify activity counts, processor 46 may be able to more accurately determine the extent of patient activity for both high impact, low frequency and low impact, high frequency activities. Processor 46 may store the determined number of activity counts in memory 48 as an activity level. In some embodiments, IMD 14 may include a filter (not shown), or processor 46 may apply a digital filter, that passes a band of the accelerometer signal from approximately 0.1 Hz to 10 Hz, e.g., the portion of the signal that reflects patient activity.

Processor 46 may identify postures and record activity levels continuously or periodically, e.g., one sample of the signals output by sensors 40 every minute or continuously for ten minutes each hour. Further, processor 46 need not identify postures and record activity levels with the same frequency. For example, processor 46 may identify postures less frequently then activity levels are determined.

In some embodiments, processor 46 limits recording of postures and activity levels to relevant time periods, i.e., when patient 12 is awake or likely to be awake, and therefore likely to be active. For example, patient 12 may indicate via patient programmer 26 when patient is going to sleep or has awoken. Processor 46 may receive these indications via a telemetry circuit 50 of IMD 14, and may suspend or resume recording of posture events based on the indications. In other embodiments, processor 46 may maintain a real-time clock, and may record posture events based on the time of day indicated by the clock, e.g., processor 46 may limit posture event recording to daytime hours. Alternatively, processor 46 may wirelessly interact with a real-time clock within the patient programmer.

In some embodiments, processor 46 may monitor one or more physiological parameters of patient 12 via signals generated by sensors 40, and may determine when patient 12 is attempting to sleep or asleep based on the physiological parameters. For example, processor 46 may determine when patient 12 is attempting to sleep by monitoring the posture of patient 12 to determine when patient 12 is recumbent.

In order to determine whether patient 12 is asleep, processor 46 may monitor any one or more physiological parameters that discernibly change when patient 12 falls asleep, such as activity level, heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. Processor 46 may additionally or alternatively monitor the variability of one or more of these physiological parameters, such as heart rate and respiration rate, which may discernible change when patient 12 is asleep. Further details regarding monitoring physiological parameters to identify when a patient is attempting to sleep and when the patient is asleep may be found in a commonly-assigned and co-pending U.S. patent application by Kenneth Heruth and Keith Miesel, entitled "DETECTING SLEEP," which was assigned Ser. No. 11/081,786 and filed Mar. 16, 2005, and is incorporated herein by reference in its entirety.

In other embodiments, processor 46 may record postures and activity levels in response to receiving an indication from patient 12 via patient programmer 26. For example, processor 46 may record postures and activity levels during times when patient 12 believes the therapy delivered by IMD 14 is ineffective and/or the symptoms experienced by patient 12 have worsened. In this manner, processor 46 may limit data collection to periods in which more probative data is likely to be collected, and thereby conserve a battery and/or storage space within memory 48.

Although described above with reference to an exemplary embodiment in which sensors 40 include accelerometers, sensors 40 may include any of a variety of types of sensors that generate signals as a function of patient posture and/or activity. For example, sensors 40 may include orthogonally aligned gyros or magnetometers that generate signals that indicate the posture of patient 12.

Other sensors 40 that may generate a signal that indicates the posture of patient 12 include electrodes that generate an electromyogram (EMG) signal, or bonded piezoelectric crystals that generate a signal as a function of contraction of muscles. Such sensors 40 may be implanted in the legs, buttocks, abdomen, or back of patient 12, as described above. The signals generated by such sensors when implanted in these locations may vary based on the posture of patient 12, e.g., may vary based on whether the patient is standing, sitting, or lying down.

Further, the posture of patient 12 may affect the thoracic impedance of the patient. Consequently, sensors 40 may include an electrode pair, including one electrode integrated with the housing of IMD 14 and one of electrodes 42, that generates a signal as a function of the thoracic impedance of patient 12, and processor 46 may detect the posture or posture changes of patient 12 based on the signal. The electrodes of the pair may be located on opposite sides of the patient's thorax. For example, the electrode pair may include one of electrodes 42 located proximate to the spine of a patient for delivery of SCS therapy, and IMD 14 with an electrode integrated in its housing may be implanted in the abdomen of patient 12.

Additionally, changes of the posture of patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMD 14 wirelessly or via lead 16. CSF pressure changes associated with posture changes may be particularly evident within the brain of the patient, e.g., may be particularly apparent in an intracranial pressure (ICP) waveform.

Other sensors 40 that output a signal as a function of patient activity may include one or more bonded piezoelectric crystals, mercury switches, or gyros that generate a signal as a function of body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of patient 12 to detect muscle activity associated with walking, running, or the like. The electrodes may be coupled to IMD 14 wirelessly or by leads 16 or, if IMD 14 is implanted in these locations, integrated with a housing of IMD 14.

However, bonded piezoelectric crystals located in these areas generate signals as a function of muscle contraction in addition to body motion, footfalls or other impact events. Consequently, use of bonded piezoelectric crystals to detect activity of patient 12 may be preferred in some embodiments in which it is desired to detect muscle activity in addition to body motion, footfalls, or other impact events. Bonded piezoelectric crystals may be coupled to IMD 14 wirelessly or via leads 16, or piezoelectric crystals may be bonded to the can of IMD 14 when the IMD is implanted in these areas, e.g., in the back, chest, buttocks or abdomen of patient 12.

Further, in some embodiments, processor 46 may monitor one or more signals that indicate a physiological parameter of patient 12, which in turn varies as a function of patient activity. For example, processor 46 may monitor a signal that indicates the heart rate, ECG morphology, respiration rate, respiratory volume, core or subcutaneous temperature, or muscular activity of the patient, and sensors 40 may include any known sensors that output a signal as a function of one or more of these physiological parameters. In such embodiments, processor 46 may periodically determine a heart rate, value of an ECG morphological feature, respiration rate, respiratory volume, core temperature, or muscular activity level of patient 12 based on the signal. The determined values of these parameters may be mean or median values.

In some embodiments, processor 46 compares a determined value of such a physiological parameter to one or more thresholds or a look-up table stored in memory to determine a number of activity counts, and stores the determined number of activity counts in memory 48 as a determined activity level. In other embodiments, processor 46 may store the determined physiological parameter value as a determined activity level. The use of activity counts, however, may allow processor 46 to determine an activity level based on a plurality of signals generated by a plurality of sensors 40. For example, processor 46 may determine a first number of activity counts based on a sample of an accelerometer signal and a second number of activity counts based on a heart rate determined from an electrogram signal at the time the accelerometer signal was sampled. Processor 46 may determine an activity level by calculating the sum or average, which may be a weighted sum or average, of first and second activity counts.

As described above, the invention is not limited to embodiments in which IMD 14 determines postures or activity levels. In some embodiments, processor 46 may periodically store samples of the signals generated by sensors 40 in memory 48, rather than postures and activity levels, and may associate those samples with the current therapy parameter set.

Figure 3:
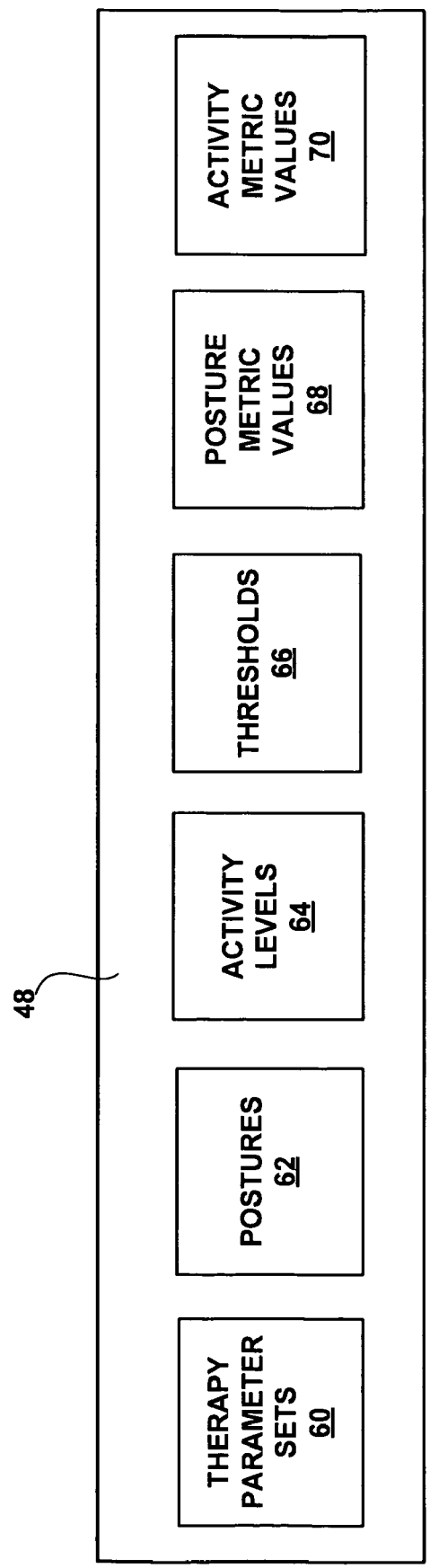
FIG. 3 is a block diagram illustrating an example memory of the implantable medical device of FIG. 1.

FIG. 3 illustrates memory 48 of IMD 14 in greater detail. As shown in FIG. 3, memory 48 stores information describing a plurality of therapy parameter sets 60. Therapy parameter sets 60 may include parameter sets specified by a clinician using clinician programmer 20. Therapy parameter sets 60 may also include parameter sets that are the result of patient 12 changing one or more parameters of one of the preprogrammed therapy parameter sets. For example, patient 12 may change parameters such as pulse amplitude, frequency or pulse width.

Memory 48 also stores postures 62 or postural transitions identified by processor 46. When processor 46 identifies a posture 62 or postural transition as discussed above, processor 46 associates the posture or postural transition with the current one of therapy parameter sets 60, e.g., the one of therapy parameter sets 60 that processor 46 is currently using to control delivery of therapy by therapy module 44 to patient 12. For example, processor 46 may store determined postures 62 within memory 48 with an indication of the parameter sets 60 with which they are associated. In other embodiments, processor 46 stores samples (not shown) of signals generated by sensors 40 as a function of posture within memory 48 with an indication of the parameter sets 60 with which they are associated.

Memory 48 also stores the activity levels 64 determined by processor 46. When processor 46 determines an activity level as discussed above, processor 46 associates the determined activity level 64 with the current therapy parameter set 60, e.g., the one of therapy parameter sets 60 that processor 46 is currently using to control delivery of therapy by therapy module 44 to patient 12. In some embodiments, for example, processor 46 may store determined activity levels 64 within memory 48 with an indication of the posture 62 and parameter sets 60 with which they are associated. In other embodiments, processor 46 stores samples (not shown) of signals generated by sensors 40 as a function of patient activity within memory 48 with an indication of the posture 62 and parameter sets 60 with which they are associated.

In some embodiments, processor 46 determines a value of one or more activity metrics for each of therapy parameter sets 60 based on the activity levels 64 associated with the parameter sets 60. In such embodiments, processor 46 may store the determined activity metric values 70 within memory 48 with an indication as to which of therapy parameter sets 60 the determined values are associated with. For example, processor 46 may determine a mean or median of activity levels associated with a therapy parameter set, and store the mean or median activity level as an activity metric value 70 for the therapy parameter set.

In embodiments in which activity levels 64 comprise activity counts, processor 46 may store, for example, an average number of activity counts per unit time as an activity metric value. An average number of activity counts over some period substantially between ten and sixty minutes, for example, may provide a more accurate indication of activity than an average over shorter periods by ameliorating the effect of transient activities on an activity signal or physiological parameters. For example, rolling over in bed may briefly increase the amplitude of an activity signal and a heart rate, possibly skewing the efficacy analysis.

In other embodiments, processor 46 may compare a mean or median activity level to one or more threshold values, and may select an activity metric value from a predetermined scale of activity metric values based on the comparison. The scale may be numeric, such as activity metric values from 1-10, or qualitative, such as low, medium or high activity. The scale of activity metric values may be, for example, stored as a look-up table within memory 48. Processor 46 stores the activity metric value 70 selected from the scale within memory 48.

In some embodiments, processor 46 compares each activity level 64 associated with a therapy parameter set 60 to one or more threshold values. Based on the comparison, processor 46 may determine percentages of time above and/or below the thresholds, or within threshold ranges. Processor 46 may store the one or more determined percentages within memory 48 as one or more activity metric values 70 for that therapy parameter set. In other embodiments, processor 46 compares each activity level 64 associated with a therapy parameter set 60 to a threshold values, and determines an average length of time that consecutively recorded activity levels 64 remained above the threshold as an activity metric value 70 for that therapy parameter set.

In some embodiments, processor 46 determines a plurality of activity metric values for each of the plurality of therapy parameter sets, and determines an overall activity metric value for a parameter set based on the values of the individual activity metrics for that parameter set. For example, processor 46 may use the plurality of individual activity metric values as indices to identify an overall activity metric value from a look-up table stored in memory 48. Processor 46 may select the overall metric value from a predetermined scale of activity metric values, which may be numeric, such as activity metric values from 1-10, or qualitative, such as low, medium or high activity.

Further, as discussed above, processor 46 may identify the plurality of postures assumed by patient 12 over the times that a therapy parameter set was active based on the postures 62 associated with that therapy parameter set. In such embodiments, processor 46 may determine a plurality of values of an activity metric for each therapy parameter set and posture, e.g., a value of the activity metric for each parameter set/posture pair. Processor 46 may determine an activity metric value 70 for a parameter set/posture pair based on the activity levels 64 associated with the therapy parameter set and the posture, e.g., the activity levels 64 collected while that therapy parameter set was active and the patient 12 was in that posture.

In some embodiments, processor 46 also determines a value of one or more posture metrics for each of therapy parameter sets 60 based on the postures 62 associated with the parameter sets 60. Processor 46 may store the determined posture metric values 68 within memory 48 with an indication as to which of therapy parameter sets 60 the determined values are associated with. For example, processor 46 may determine an amount of time that patient 12 was in a posture when a therapy parameter set 60 was active, e.g., an average amount of time over a period of time such as an hour, as a posture metric 68 for the therapy parameter set 60. Processor 46 may additionally or alternatively determine percentages of time that patient 12 assumed one or more postures while a therapy parameter set was active as a posture metric 68 for the therapy parameter set 60. As another example, processor 46 may determine an average number of transitions over a period of time, such as an hour, when a therapy parameter set 60 was active as a posture metric 68 for the therapy parameter set 60.

In some embodiments, processor 46 determines a plurality of posture metric values for each of the plurality of therapy parameter sets 60, and determines an overall posture metric value for a parameter set based on the values of the individual posture metrics for that parameter set. For example, processor 46 may use the plurality of individual posture metric values as indices to identify an overall posture metric value from a look-up table stored in memory 48. Processor 46 may select the overall posture metric value from a predetermined scale of posture metric values, which may be numeric, such as posture metric values from 1-10.

The various thresholds described above as being used by processor 46 to determine activity levels 62, postures 64, posture metric values 68, and activity metric values 70 may be stored in memory 48 as thresholds 66, as illustrated in FIG. 3. In some embodiments, threshold values 66 may be programmable by a user, e.g., a clinician, using one of programmers 20, 26. Further, the clinician may select which activity metric values 70 and posture metric values 68 are to be determined via one of programmers 20, 26.

As shown in FIG. 2, IMD 14 includes a telemetry circuit 50, and processor 46 communicates with programmers 20, 26, or another computing device, via telemetry circuit 50. In some embodiments, processor 46 provides information identifying therapy parameter sets 60, postures 62, posture metric values 68, and activity metric values 70 associated with the parameter sets to one of programmers 20, 26, or the other computing device, and the programmer or other computing device displays a list of therapy parameter sets 60 and associated postures 62 and metric values 68, 70. In other embodiments, as will be described in greater detail below, processor 46 does not determine metric values 68, 70. Instead, processor 46 provides postures 62 and activity levels 64 to the programmer 20, 26 or other computing device via telemetry circuit 50, and the programmer or computing device determines metric values 68, 70 for display to the clinician. Further, in other embodiments, processor 46 provides samples of signals generated by sensors 40 to the programmer 20, 26 or other computing device via telemetry circuit 50, and the programmer or computing device may determine postures 62, activity levels 64, and metric values 68, 70 based on the samples. Some external medical device embodiments of the invention include a display, and a processor of such an external medical device may both determine metric values 68, 70 and display a list of therapy parameter sets 60 and associated metric values to a clinician.

Figure 4:
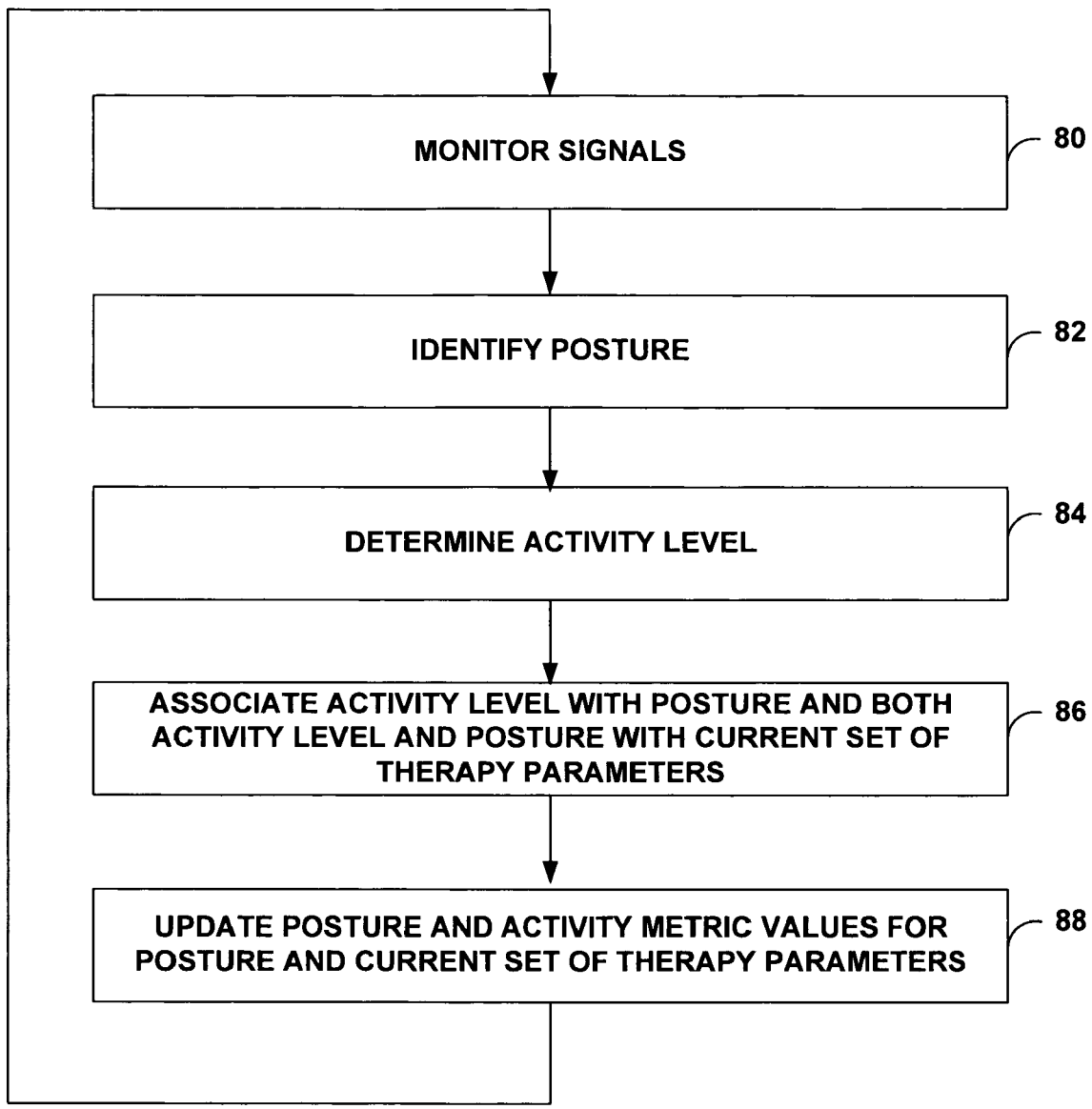
FIG. 4 is a flow diagram illustrating an example method for collecting posture and activity information that may be employed by an implantable medical device.

FIG. 4 is a flow diagram illustrating an example method for collecting posture and activity information that may be employed by IMD 14. IMD 14 monitors one or more signals generated by sensors 40 (80). For example, IMD 14 may monitor signals generated by a plurality of orthogonally aligned accelerometers, as described above. Each of the accelerometers may be substantially aligned with a respective axis of the body of patient 12.

IMD 14 identifies a posture 62 (82). For example, IMD 14 may identify a current posture of patient 12 at a time when the signals generated by sensors 40 are sampled, or may identify the occurrence of a transition between postures. IMD 14 also determines an activity level 64 (84). For example, IMD 14 may determine a number of activity counts based on the one or more of the accelerometer signals, as described above.

IMD 14 identifies the current therapy parameter set 60, and associates the identified posture 62 with the current therapy parameter set 60 (86). For example, IMD 14 may store information describing the identified posture 62 within memory 48 with an indication of the current therapy parameter set 60. IMD 14 also associates the determined activity level 64 with the posture patient 12 is currently in, e.g., the most recently identified posture 62, and the current therapy parameter set 60 (86). For example, IMD 14 may store the determined activity level 64 in memory 48 with an indication of the current posture 62 and therapy parameter set 60. IMD 14 may then update one or more posture and/or activity metric values 68, 70 associated with the current therapy parameter set 60 and posture 62, e.g., the current therapy parameter set/posture pair, as described above (88).

IMD 14 may periodically perform the example method illustrated in FIG. 4, e.g., may periodically monitor the signals generated by sensors 40 (80), determine postures 62 and activity levels 64 (82, 84), and associate the determined postures 62 and activity levels 64 with a current therapy parameter set 60 (86). Postures 62 and activity levels 64 need not be determined with the same frequency. Further, as described above, IMD 14 may only perform the example method during daytime hours, or when patient is awake and not attempting to sleep, and/or only in response to an indication received from patient 12 via patient programmer 20. Additionally, IMD 14 need not update metric values 68, 70 each time a posture 62 or activity level 64 is determined. In some embodiments, for example, IMD 14 may store postures 62 and activity levels 64 within memory 48, and may determine the metric values 68, 70 upon receiving a request for the values from one of programmers 20, 26.

Further, in some embodiments, as will be described in greater detail below, IMD 14 does not determine the metric values 68, 70, but instead provides postures 62 and activity levels 64 to a computing device, such as clinician programmer 20 or patient programmer 26. In such embodiments, the computing device determines the metric values associated with each of the therapy parameter set/posture pair. Additionally, as described above, IMD 14 need not determine postures 62 and activity levels 64, but may instead store samples of the signals generated by sensors 40. In such embodiments, the computing device may determine postures, activity levels, and metric values based on the samples.

Figure 5:
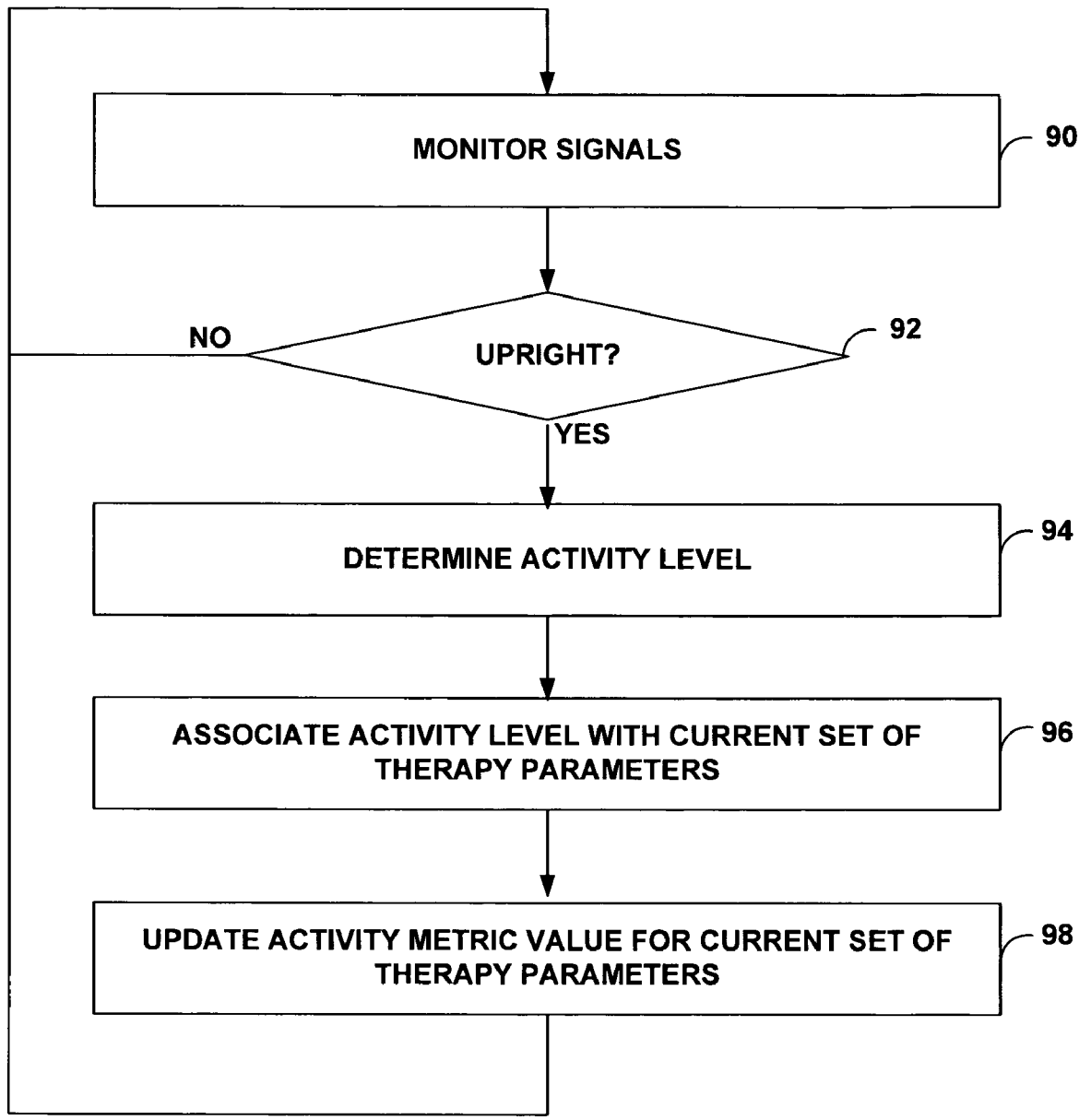
FIG. 5 is a flow diagram illustrating an example method for collecting activity information based on patient posture that may be employed by an implantable medical device.

FIG. 5 is a flow diagram illustrating an example method for collecting activity information based on patient posture that may be employed by IMD 14. In some embodiments, IMD 14 need not store postures 62, determine posture metrics 68, or associate activity levels 64 with particular postures. Rather, as illustrated in FIG. 5, IMD 14 may limit activity information collection, e.g., determination of activity levels 64, to times when patient 12 is in a target posture, e.g., a posture of interest. A target posture may be, for example, upright, e.g., standing or sitting, or may be only standing. In some cases, the activity of patient 12 while in such target postures may be particularly indicative of the effectiveness of a therapy.

IMD 14 monitors one or more signals generated by sensors 40 (90). For example, IMD 14 may monitor signals generated by a plurality of orthogonally aligned accelerometers, as described above. Each of the accelerometers may be substantially aligned with a respective axis of the body of patient 12.

IMD 14 determines whether patient 12 is upright based upon the signals (92). If patient 12 is upright, IMD 14 determines an activity level 64 (94), and associates the determined activity level 64 with a current set of therapy parameters 60 (96). For example, IMD 14 may determine a number of activity counts based on the one or more of the accelerometer signals, as described above, and may store the determined activity level 64 in memory 48 with an indication of the current therapy parameter set 60. IMD 14 may then update one or more activity metric values 68 associated with the current therapy parameter set 60 (98).

As is the case with the example method illustrated in FIG. 4, IMD 14 may periodically perform the example method illustrated in FIG. 5, e.g., may periodically monitor the signals generated by sensors 40 (90), determine whether patient 12 is in a posture of interest (92), determine activity levels 64 when patient 12 is in the posture of interest (94), and associate the determined activity levels 64 with a current therapy parameter set 60 (96). Further, as described above, IMD 14 may only perform the example method during daytime hours, or when patient is awake and not attempting to sleep, and/or only in response to an indication received from patient 12 via patient programmer 20. Additionally, IMD 14 need not update activity metric values 70 each time an activity level 64 is determined. In some embodiments, for example, IMD 14 may store activity levels 64 within memory, and may determine the activity metric values 70 upon receiving a request for the values from one of programmers 20, 26.

Further, in some embodiments, as will be described in greater detail below, IMD 14 does not determine the activity metric values 70, but instead provides activity levels 64 to a computing device, such as clinician programmer 20 or patient programmer 26. In such embodiments, the computing device determines the activity metric values associated with each of the therapy parameter sets. Additionally, as described above, IMD 14 need not determine postures 62 and activity levels 64, but may instead store samples of the signals generated by sensors 40. In such embodiments, the computing device may determine postures, activity levels, and activity metric values based on the samples.

Figure 6:
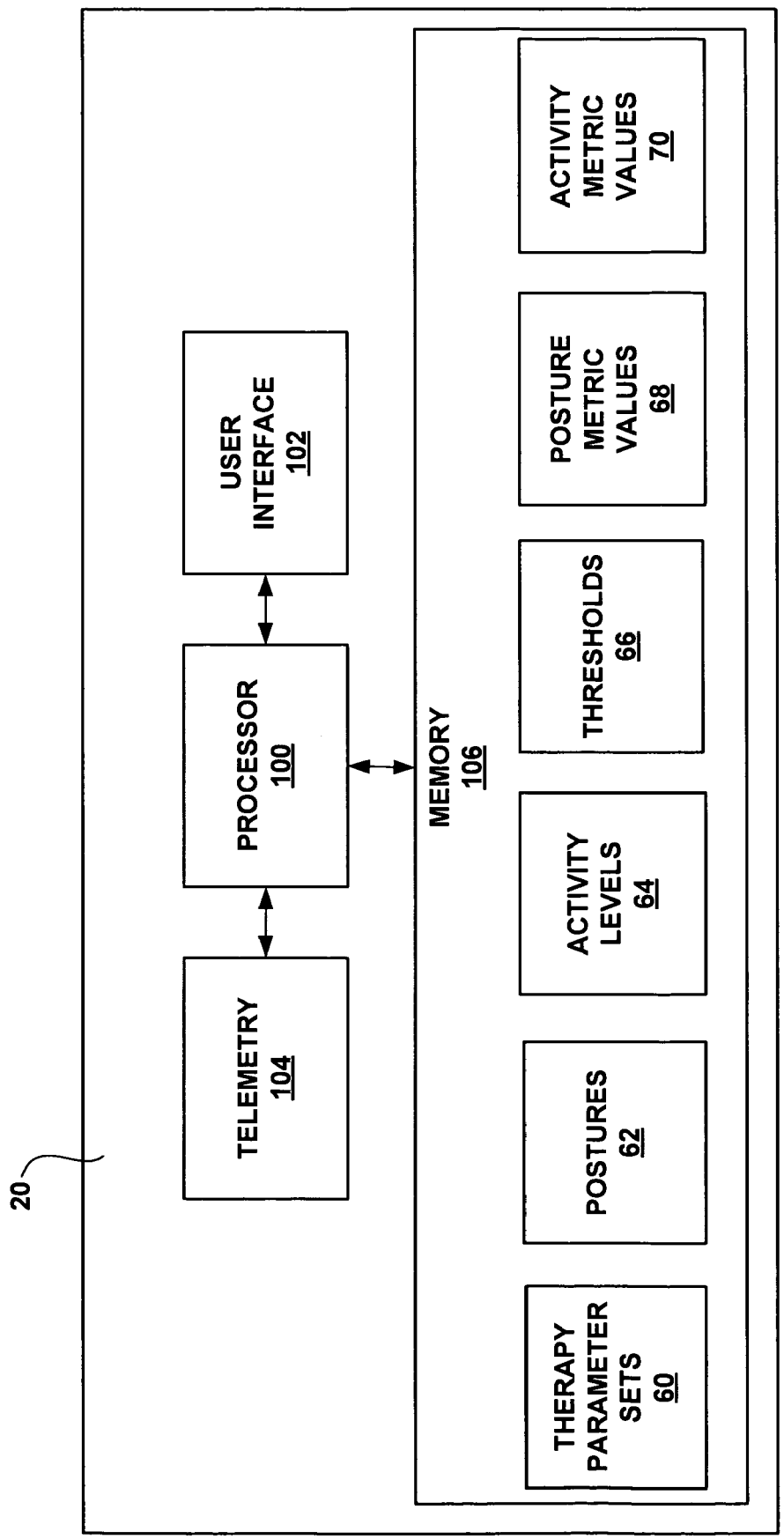
FIG. 6 is a block diagram illustrating an example clinician programmer.

FIG. 6 is a block diagram illustrating clinician programmer 20. A clinician may interact with a processor 100 via a user interface 102 in order to program therapy for patient 12, e.g., specify therapy parameter sets. Processor 100 may provide the specified therapy parameter sets to IMD 14 via telemetry circuit 104.

At another time, e.g., during a follow up visit, processor 100 may receive information identifying a plurality of therapy parameter sets 60 from IMD 14 via telemetry circuit 104, which may be stored in a memory 106. The therapy parameter sets 60 may include the originally specified parameter sets, and parameter sets resulting from manipulation of one or more therapy parameters by patient 12 using patient programmer 26. In some embodiments, processor 100 also receives posture and activity metric values 68, 70 associated with the therapy parameter sets 60, and stores the metric values in memory 106. In other embodiments, processor 100 may receive postures 62 and activity levels 64 associated with the therapy parameter sets 60, and determine values 68, 70 of one or more metrics for each of the plurality of therapy parameter sets 60 using any of the techniques described above with reference to IMD 14 and FIGS. 2 and 3. In still other embodiments, processor 100 receives samples of signals generated by sensors 40, either from IMD 14, from a separate monitor that includes or is coupled to sensors 40, or directly from sensors 40, and determines postures 62, activity levels 64 and metric values 68, 70 based on signals using any of the techniques described above with reference to IMD 14 and FIGS. 2 and 3.

Upon receiving or determining posture and activity metric values 68, 70, processor 100 may generate a list of the therapy parameter sets 60 and associated metric values 68, 70, and present the list to the clinician. User interface 102 may include display 22, and processor 100 may display the list via display 22. The list of therapy parameter sets 60 may be ordered according to a metric value, and where a plurality of metric values are associated with each of the parameter sets, the list may be ordered according to the values of the metric selected by the clinician. Processor 100 may also present other posture or activity information to a user, such as a trend diagram of activity or posture over time, or a histogram, pie chart, or other illustration of percentages of time that patient 12 was within certain postures 62, or activity levels 64 were within certain ranges. Processor 100 may generate such charts or diagrams using postures 62 and activity levels 64 associated with a particular one of the therapy parameter sets 60, or all of the postures 62 and activity levels 64 recorded by IMD 14.

User interface 102 may include display 22 and keypad 24, and may also include a touch screen or peripheral pointing devices as described above. Processor 100 may include a microprocessor, a controller, a DSP, an ASIC, an FPGA, discrete logic circuitry, or the like. Memory 106 may include program instructions that, when executed by processor 100, cause clinician programmer 20 to perform the functions ascribed to clinician programmer 20 herein. Memory 106 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

FIG. 7 illustrates an example list 110 of therapy parameter sets 60 and associated metric values 68, 70 that may be presented by clinician programmer 20. Each row of example list 110 includes an identification of one of therapy parameter sets 60, the parameters of the therapy parameter set, and an identification of the postures assumed by patient 12 when the parameter set was active, e.g., the categories of postures 62 associated with the parameter set. In the illustrated example, each of the listed therapy parameter sets 60 is associated with two postural categories, i.e., upright and recumbent.

Each of the listed therapy parameter sets is also associated with two values 70 for each of two activity metrics, i.e., an activity metric value 70 for each posture associated with the therapy parameter set. The activity metrics illustrated in FIG. 7 are a percentage of time active, and an average number of activity counts per hour. IMD 14 or programmer 20 may determine the average number of activity counts per hour for one of the illustrated therapy parameter set/posture pairs by identifying the total number of activity counts associated with the parameter set and the posture, and the total amount of time that patient was in that posture while IMD 14 was using the parameter set. IMD 14 or programmer 20 may determine the percentage of time active for one of the illustrated therapy parameter set/posture pairs by comparing each activity level associated with the parameter set and posture to an "active" threshold, and determining the percentage of activity levels above the threshold. As illustrated in FIG. 7, IMD 14 or programmer 20 may also compare each activity level for the therapy parameter/posture pair set to an additional, "high activity" threshold, and determine a percentage of activity levels above that threshold.

As illustrated in FIG. 7, list 110 may also include a posture metric 68. In the illustrated example, list 110 includes as posture metrics 68 for each therapy parameter set the percentage of time that patient 12 was in each posture when the therapy parameter set was active. Programmer 20 may order list 110 according to a user-selected one of the metrics 68, 70.

Figure 8:
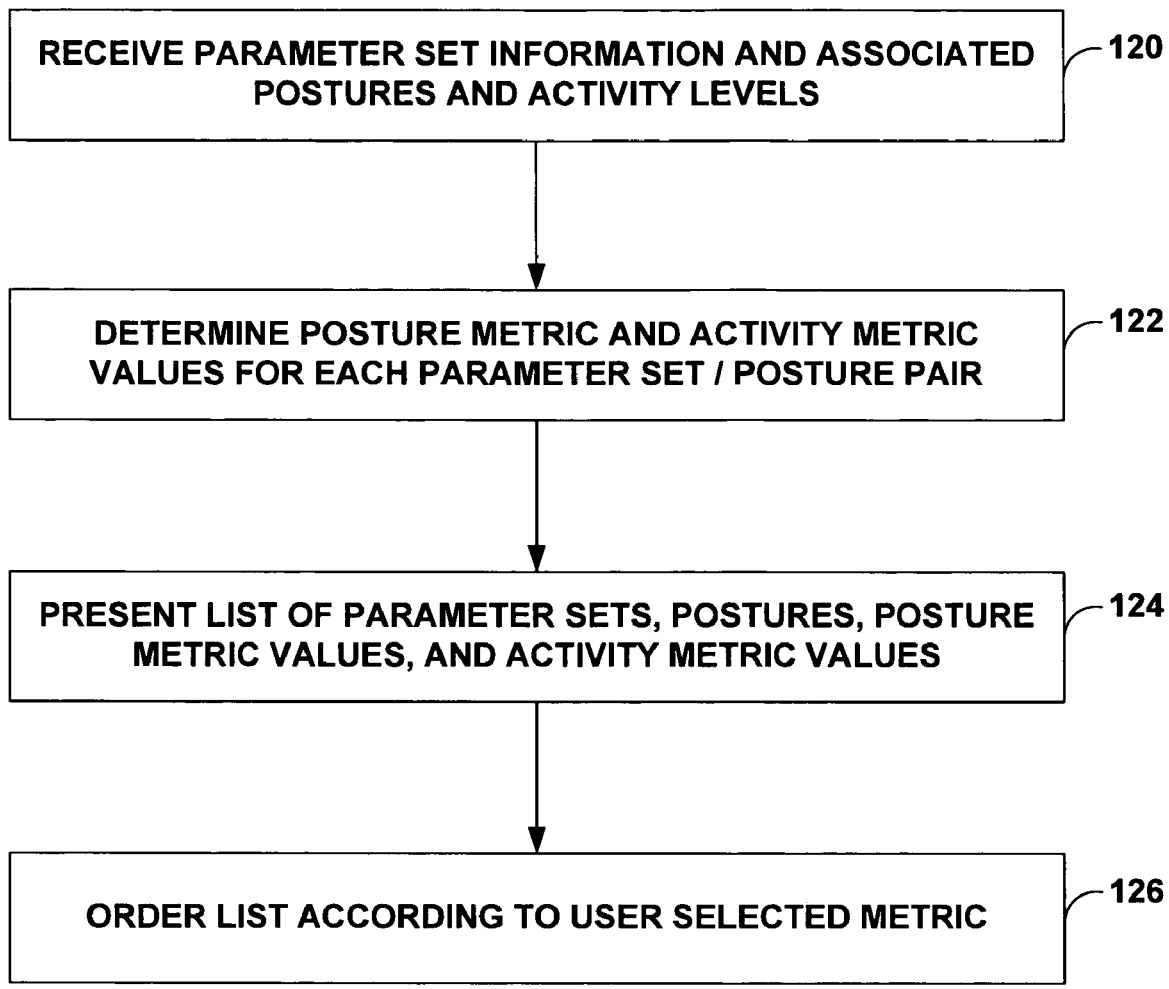
FIG. 8 is a flow diagram illustrating an example method for displaying a list of therapy parameter sets and associated posture and activity metric values that may be employed by a clinician programmer.

FIG. 8 is a flow diagram illustrating an example method for displaying a list of therapy parameter sets 60 and associated metric values 68, 70 that may be employed by a clinician programmer 20. Although described with reference to clinician programmer 20, patient programmer 26 or another computing device may perform the method illustrated by FIG. 6.

Programmer 20 receives information identifying therapy parameter sets 60 and associated postures 62 and activity levels 64 from IMD 14 (120). Programmer 20 then determines one or more posture and activity metric values 68, 70 for each of the therapy parameter sets based on the postures 62 and activity levels 64 associated with the therapy parameter sets (122). In other embodiments, IMD 14 determines the metric values, and provides them to programmer 20, or provides samples of signals associated with therapy parameter sets to programmer 20 for determination of metric values, as described above. After receiving or determining metric values 68, 70, programmer 20 presents a list 110 of therapy parameter sets 60 and associated metric values 68, 70 to the clinician, e.g., via display 22 (124). Programmer 20 may order list 110 of therapy parameter sets 60 according to the associated metric values, and the clinician may select according to which of a plurality of metrics list 110 is ordered via a user interface 82 (126).

In some embodiments, as discussed above, one or more of IMD 14, programmers 20, 26, or another computing device may conduct a sensitivity analysis of one or more posture and/or activity metric values 68, 70 to identify one or more therapy parameter sets for use in delivering therapy to patient 12. The sensitivity analysis may be performed as an alternative or in addition to presenting posture and activity information to a user for evaluation of therapy parameter sets.

The IMD, programmer, or the other computing device may perform the sensitivity analysis to identify a value for each therapy parameters that defines substantially maximum or minimum posture and/or activity metric values. In other words, the sensitivity analysis identifies therapy parameter values that yield the "best" metric values. The IMD, programmer, or other computing device then identifies one or more baseline therapy parameter sets that include the identified parameter values, and stores the baseline therapy parameter sets as therapy parameter sets 60 or separately within memory 48 of IMD 14. IMD 14 may then deliver stimulation according to the baseline therapy parameter sets. The baseline therapy parameter sets include the values for respective therapy parameters that produced the best activity and/or posture metric values.

Figure 9:
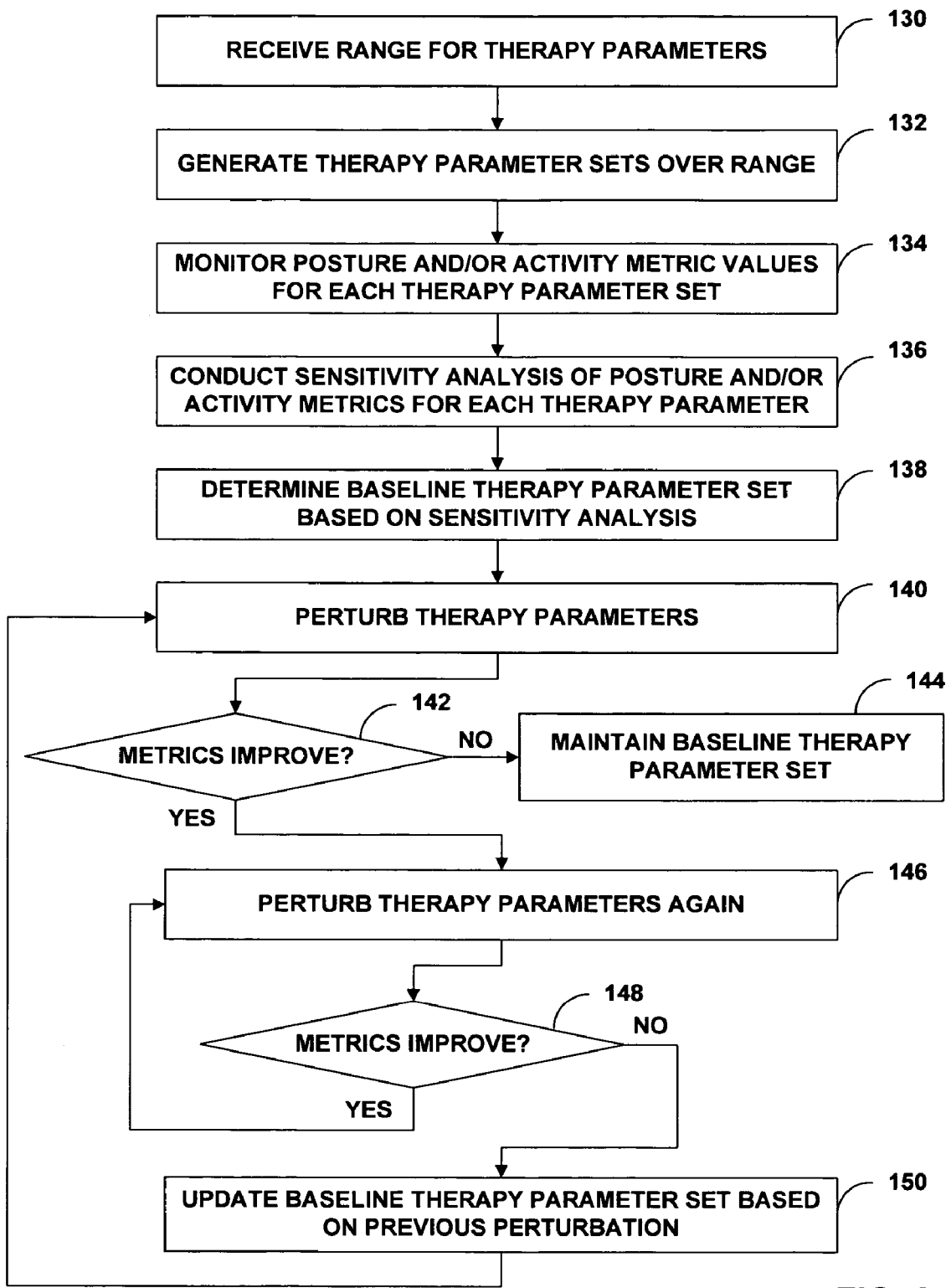
FIG. 9 is a flow diagram illustrating an example method for identifying a therapy parameter set based on collected posture and/or activity information that may be employed by a medical device.

In some embodiments, the IMD, programmer, or other computing device may adjust the therapy delivered by IMD 14 based on a change in the activity or posture metric values 68, 70. In particular, the IMD, programmer, or other computing device may perturb one or more therapy parameters of a baseline therapy parameter set, such as pulse amplitude, pulse width, pulse rate, duty cycle, and duration, to determine if the current posture and/or activity metric values improve or worsen during perturbation. In some embodiments, values of the therapy parameters may be iteratively and incrementally increased or decreased until substantially maximum or minimum values of the posture and/or activity metric are again identified FIG. 9 is a flow diagram illustrating an example method for identifying a therapy parameter set, e.g., a baseline therapy parameter set, based on collected posture and/or activity information that may be employed by IMD 14. For ease of description, a number of the actions that are part of the method illustrated in FIG. 9 are described as being performed by IMD 14. However, in some embodiments, as discussed above, an external computing device, such as one of programmers 20, 26, and more particularly the processor of such a computing device, may perform one or more of the activities attributed to IMD 14 below.

IMD 14 receives a therapy parameter range for therapy parameters (130) from a clinician using clinician programmer 20 via telemetry circuit 50. The range may include minimum and maximum values for each of one or more individual therapy parameters, such as pulse amplitude, pulse width, pulse rate, duty cycle, duration, dosage, infusion rate, electrode placement, and electrode selection. The range may be stored in memory 48, as described in reference to FIG. 3.

Processor 46 then randomly or non-randomly generates a plurality of therapy parameter sets 60 with individual parameter values selected from the range (132). The generated therapy parameter sets 60 may substantially cover the range, but do not necessarily include each and every therapy parameter value within the therapy parameter range, or every possible combination of therapy parameters within the range. The generated therapy parameter sets 60 may also be stored in memory 48.

IMD 14 monitors at least one posture or activity metric 68, 70 of patient 12 for each of the randomly or non-randomly generated therapy parameter sets 60 spanning the range (134). The values of the metrics corresponding to each of the therapy parameter sets 60 may be stored in memory 48 of IMD 14, as described above. IMD 14 then conducts a sensitivity analysis of the one or more posture and/or activity metrics for each of the therapy parameters, e.g., each of pulse amplitude, pulse width, pulse rate and electrode configuration (136). The sensitivity analysis determines a value for each of the therapy parameters that produced a substantially maximum or minimum value of the one or more metrics. One or more baseline therapy parameter sets are then determined based on the therapy parameter values identified by the sensitivity analysis (138). The baseline therapy parameter sets include combinations of the therapy parameter values individually observed to produce substantially maximum or minimum values of the one or more posture or activity metrics 68, 70. The baseline therapy parameter sets may also be stored with therapy parameters sets 60 in memory 48. In some embodiments, the baseline therapy parameter sets may be stored separately from the generated therapy parameter sets.

After this initial baseline therapy parameter set identification phase of the example method, IMD 14 may control delivery of the therapy based on the baseline therapy parameter sets. Periodically during the therapy, IMD 14 checks to ensure that the baseline therapy parameter sets continues to define substantially maximum or minimum posture and/or activity metric values for patient 12. IMD 14 first perturbs at least one of the therapy parameter values of a baseline therapy parameter set (140). The perturbation comprises incrementally increasing and/or decreasing the therapy parameter value, or changing electrode polarities. A perturbation period may be preset to occur at a specific time, in response to a physiological parameter monitored by the IMD, or in response to a signal from the patient or clinician. The perturbation may be applied for a single selected parameter or two or more parameters, or all parameters in the baseline therapy parameter set. Hence, numerous parameters may be perturbed in sequence. For example, upon perturbing a first parameter and identifying a value that produces a maximum or minimum metric value, a second parameter may be perturbed with the first parameter value fixed at the identified value. This process may continue for each of the parameters in a baseline therapy parameter set, and for each of a plurality of baseline therapy parameter sets.

Upon perturbing a parameter value, IMD 14 then compares a value of the one or more metrics defined by the perturbed therapy parameter set to a corresponding value of the metric defined by the baseline therapy parameter set during the initial baseline identification phase (142). If the metric values do not improve with the perturbation, IMD 14 maintains the unperturbed baseline therapy parameter set values (144). If the metric values do improve with the perturbation, IMD 14 perturbs the therapy parameter value again (146) in the same direction that defined the previous improvement in the metric values. IMD 14 compares a value of the metrics defined by the currently perturbed therapy parameter set to the metric values defined by the therapy parameter set of the previous perturbation (148). If the metric values do not improve, IMD 14 updates the baseline therapy parameter set based on the therapy parameter values from the previous perturbation (150). If the metric values improve again, IMD 14 continues to perturb the therapy parameter value (146).

Periodically checking the values of one or more metrics for the baseline therapy parameter set during this perturbation phase of the example method allows IMD 14 to consistently deliver a therapy to patient 12 that defines a substantially maximum or minimum posture and/or activity metric values 68, 70. This may allow the patient's symptoms to be continually managed even as the patient's physiological parameters and symptoms change.

Various embodiments of the invention have been described. However, one skilled in the art will recognize that various modifications may be made to the described embodiments without departing from the scope of the invention. For example, the invention may be embodied as a computer-readable medium that includes instructions to cause a processor to perform any of the methods described herein.

As another example, although described herein primarily in the context of treatment of pain with an implantable neurostimulator, the invention is not so limited. The invention may be embodied in any implantable medical device that delivers a therapy, such as a cardiac pacemaker or an implantable pump. Further, the invention may be implemented via an external, e.g., non-implantable, medical device. In such embodiments, the external medical device itself may include a user interface and display to present activity information to a user, such as a clinician or patient, for evaluation of therapy parameter sets.

Additionally, the invention is not limited to embodiments in which a programming device receives information from the medical device, or presents information to a user. Other computing devices, such as handheld computers, desktop computers, workstations, or servers may receive information from the medical device and present information to a user as described herein with reference to programmers 20, 26. A computing device, such as a server, may receive information from the medical device and present information to a user via a network, such as a local area network (LAN), wide area network (WAN), or the Internet. Further, in some embodiments, the medical device is an external medical device, and may itself include user interface and display to present activity information to a user, such as a clinician or patient, for evaluation of therapy parameter sets.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Posture and activity metric values collected during use of the trial neurostimulator or pump may be used by a clinician to evaluate the prospective therapy parameter sets, and select parameter sets for use by the later implanted non-trial neurostimulator or pump. The posture and activity metric values may be collected by the trial device in the manner described above with reference to IMD 14, or by a programmer 20, 26 or other computing device, as described above. After a trial period, a programmer or computing device may present a list of prospective parameter sets and associated metric values to a clinician. The clinician may use the list to identify potentially efficacious parameter sets, and may program a permanent implantable neurostimulator or pump for the patient with the identified parameter sets.

In some embodiments, a trial neurostimulator or pump, or a programmer or other external computing device, may perform a sensitivity analysis as described above on a range of therapy parameters tested by the trial neurostimulator or pump during a trialing period. A permanent implantable neurostimulator or pump may be programmed with the one or more baseline therapy parameter sets identified by the sensitivity analysis, and may periodically perturb the baseline therapy parameter sets to maintain effective therapy in the manner described above.

Additionally, as discussed above, the invention is not limited to embodiments in which the therapy delivering medical device monitors activity or posture. In some embodiments, a separate monitoring device monitors values of one or more physiological parameters of the patient instead of, or in addition to, a therapy delivering medical device. The monitor may include a processor 46 and memory 48, and may be coupled to or include sensors 40, as illustrated above with reference to IMD 14 and FIGS. 2 and 3.

The monitor may identify postures and activity levels based on the values of the monitored physiological parameter values, and determine posture and activity metric values based on the identified postures and activity levels as described herein with reference to IMD 14. Alternatively, the monitor may transmit indications of posture and activity levels to an IMD, programmer, or other computing device, which may then determine posture and activity metric values. As another alternative, the monitor may transmit recorded physiological parameter values to an IMD, programmer, or other computing device for determination of postures, activity levels, and/or posture and activity metric values.

Figure 10:
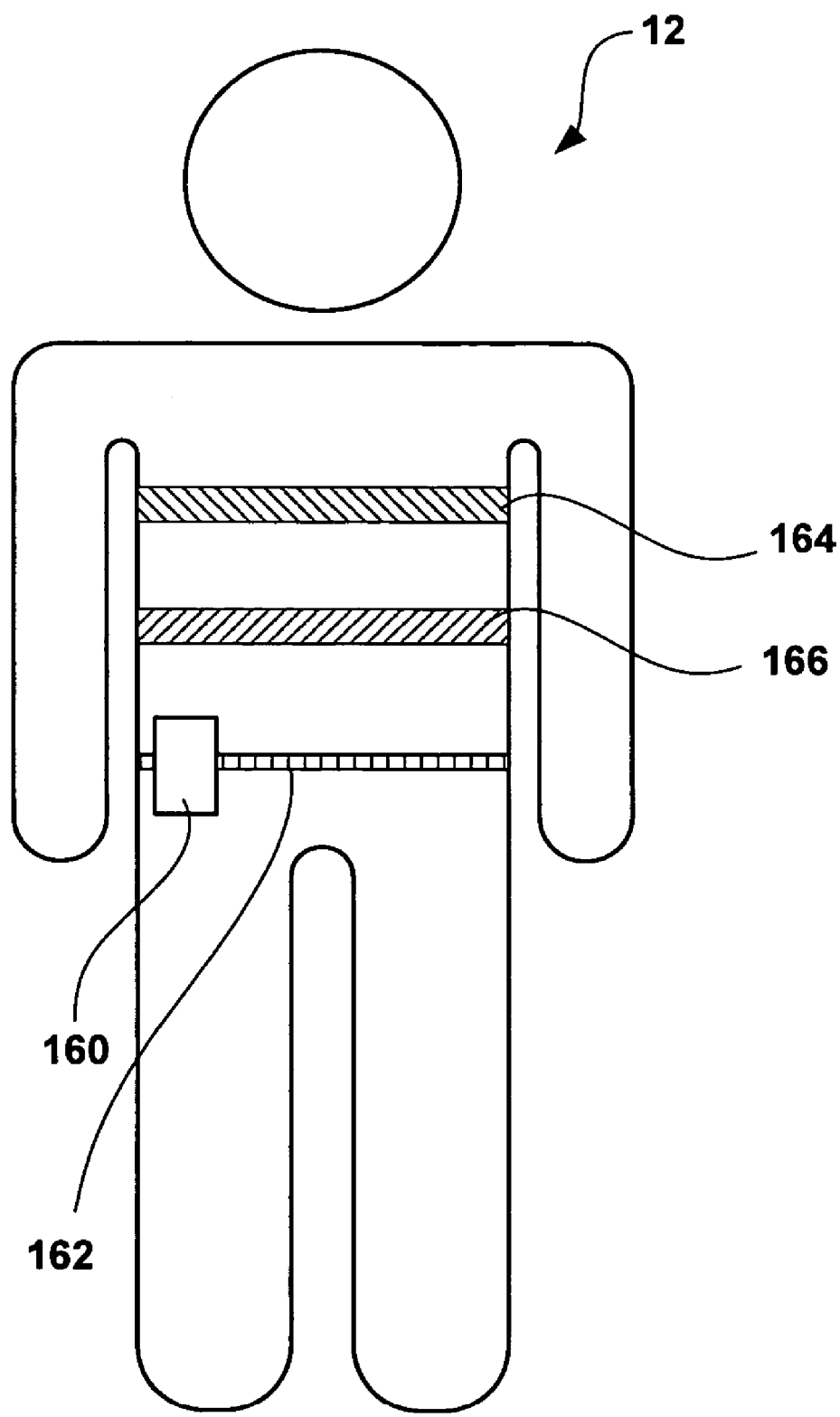
FIG. 10 is a conceptual diagram illustrating a monitor that monitors values of one or more physiological parameters of the patient.

FIG. 10 is a conceptual diagram illustrating a monitor 160 that monitors the posture and activity of the. patient instead of, or in addition to, a therapy delivering medical device. In the illustrated example, monitor 160 is configured to be attached to or otherwise carried by a belt 162, and may thereby be worn by patient 12. FIG. 10 also illustrates various sensors 40 that may be coupled to monitor 160 by leads, wires, cables, or wireless connections.

In the illustrated example, patient 12 wears an ECG belt 164. ECG belt 164 incorporates a plurality of electrodes for sensing the electrical activity of the heart of patient 12. The heart rate and, in some embodiments, ECG morphology of patient 12 may monitored by monitor 150 based on the signal provided by ECG belt 164. Examples of suitable belts 164 for sensing the heart rate of patient 12 are the "M" and "F" heart rate monitor models commercially available from Polar Electro. In some embodiments, instead of belt 160, patient 12 may wear of plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 10, patient 12 may also wear a respiration belt 166 that outputs a signal that varies as a function of respiration of the patient. Respiration belt 166 may be a plethysmograpy belt, and the signal output by respiration belt 166 may vary as a function of the changes is the thoracic or abdominal circumference of patient 12 that accompany breathing by the patient. An example of a suitable belt 166 is the TSD201 Respiratory Effort Transducer commercially available from Biopac Systems, Inc. Alternatively, respiration belt 166 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 164 and 166 may be a common belt worn by patient 12, and the relative locations of belts 164 and 166 depicted in FIG. 10 are merely exemplary.

Monitor 160 may additionally or alternatively include or be coupled to any of the variety of sensors 40 described above with reference to FIGS. 2 and 3, which output signals that vary as a function of activity level or posture. For example, monitor 160 may include or be coupled to a plurality of orthogonally aligned accelerometers, as described above.

These and other embodiments are within the scope of the following claims.

The invention claimed is:

1. A method comprising:
    monitoring a plurality of signals, each of the signals generated by a sensor as a function of at least one of activity or posture of a patient;
    periodically identifying a posture of the patient based on at least one of the signals;
    associating each of the identified postures with a therapy parameter set currently used by a medical device to deliver a therapy to a patient when the posture is identified;

periodically determining an activity level of the patient based on at least one of the signals;

associating each of the determined activity levels with a therapy parameter set currently used by a medical device to deliver a therapy to a patient when the activity level is determined and a current one of the periodically identified postures; and for each of a plurality of therapy parameter sets used by the medical device to deliver therapy to the patient, determining a value of an activity metric for each of the periodically identified postures associated with the therapy parameter set based on the activity levels associated with the posture and the therapy parameter set.

2. The method of claim 1, further comprising presenting a list of the therapy parameter sets, postures associated with the therapy parameter sets, and activity metric values associated with the postures and therapy parameter sets to a user.

3. The method of claim 2, further comprising:

determining a value of a posture metric for each of the therapy parameter sets based on the identified postures associated with the therapy parameter sets; and presenting the posture metric values to the user within the list.

4. The method of claim 1, further comprising:

conducting a sensitivity analysis of the activity metric for each of the plurality of therapy parameter sets; and determining a baseline therapy parameter set based on the sensitivity analysis.

5. The method of claim 1, further comprising:

determining a value of a posture metric for each of the therapy parameter sets based on the identified postures associated with the therapy parameter sets;

conducting a sensitivity analysis of the posture metric for each of the plurality of therapy parameter sets; and determining a baseline therapy parameter set based on the sensitivity analysis.

6. A medical system comprising:

a plurality of sensors, each of the sensors generating a signal as a function of at least one of activity or posture of a patient;

a medical device that delivers a therapy to the patient; and a processor that monitors the signals generated by the sensors, periodically identifies a posture of the patient based on at least one of the signals, associates each of the identified postures with a therapy parameter set currently used by a medical device to deliver a therapy to a patient when the posture is identified, periodically determines an activity level of the patient based on at least one of the signals, associates each of the determined activity levels with a therapy parameter set currently used by a medical device to deliver a therapy to a patient when the activity level is determined and a current one of the periodically identified postures, and, for each of a plurality of therapy parameter sets used by the medical device to deliver therapy to the patient, determines a value of an activity metric for each of the periodically identified postures associated with the therapy parameter set based on the activity levels associated with the posture and the therapy parameter set.

7. The medical system of claim 6, wherein the medical device includes the processor.

8. The medical system of claim 6, further comprising a computing device that includes the processor.

9. The medical system of claim 6, further comprising a display to present a list of the therapy parameter sets, postures associated with the therapy parameter sets, and activity metric values associated with the postures and therapy parameter sets to a user.

10. The medical system of claim 9, wherein the processor determines a value of a posture metric for each of the therapy parameter sets based on the identified postures associated with the therapy parameter sets, and the display presents the posture metric values to the user within the list.

11. The medical system of claim 6, wherein the processor conducts a sensitivity analysis of the activity metric for each of the plurality of therapy parameter sets, and determines a baseline therapy parameter set based on the sensitivity analysis.

12. The medical system of claim 6, wherein the processor determines a value of a posture metric for each of the therapy parameter sets based on the identified postures associated with the therapy parameter sets, conducts a sensitivity analysis of the posture metric for each of the plurality of therapy parameter sets, and determines a baseline therapy parameter set based on the sensitivity analysis.

13. The medical system of claim 6, wherein the sensors comprise a plurality of orthogonally aligned accelerometers.

14. The medical system of claim 6, wherein the medical device comprises at least one of an implantable neurostimulator and an implantable pump.

15. The medical system of claim 6, wherein the medical device comprises at least one of a trial neurostimulator and a trial pump.

16. A computer-readable medium comprising instructions that cause a programmable processor to:

monitor a plurality of signals, each of the signals generated by a sensor as a function of at least one of activity or posture of a patient;

periodically identify a posture of the patient based on at least one of the signals;

associate each of the identified postures with a therapy parameter set currently used by a medical device to deliver a therapy to a patient when the posture is identified;

periodically determine an activity level of the patient based on at least one of the signals;

associate each of the determined activity levels with a therapy parameter set currently used by a medical device to deliver a therapy to a patient when the activity level is determined and a current one of the periodically identified postures; and for each of a plurality of therapy parameter sets used by the medical device to deliver therapy to the patient, determine a value of an activity metric for each of the periodically identified postures associated with the therapy parameter set based on the activity levels associated with the posture and the therapy parameter set.

17. The computer-readable medium of claim 16, further comprising instructions that cause a programmable processor to present a list of the therapy parameter sets, postures associated with the therapy parameter sets, and activity metric values associated with the postures and therapy parameter sets to a user.

18. The computer-readable medium of claim 17, further comprising instructions that cause a programmable processor to:

determine a value of a posture metric for each of the therapy parameter sets based on the identified postures associated with the therapy parameter sets; and present the posture metric values to the user within the list.

19. A method comprising:
- monitoring a plurality of signals, each of the signals generated by a sensor as a function of at least one of activity or posture of a patient;
- determining whether the patient is in target posture based on at least one of the signals;
- periodically determining an activity level of the patient based on at least one of the signals when the patient is in the target posture;
- associating each of the determined activity levels with a current therapy parameter set; and
- for each of a plurality of therapy parameter sets used by the medical device to deliver therapy to the patient, determining a value of an activity metric based on the activity levels associated with the therapy parameter set.

20. The method of claim 19, further comprising presenting a list of the therapy parameter sets and activity metric values associated with the therapy parameter sets to a user.

21. A medical system comprising:
- a plurality of sensors, each of the sensors generating a signal as a function of at least one of activity or posture of a patient;
- a medical device that delivers a therapy to the patient; and
- a processor that monitors the signals generated by the sensors, periodically identifies a posture of the patient based on at least one of the signals, determines whether the patient is in target posture based on at least one of the signals, periodically determines an activity level of the patient based on at least one of the signals when the patient is in the target posture, associates each of the determined activity levels with a current therapy parameter set, and for each of a plurality of therapy parameter sets used by the medical device to deliver therapy to the patient, determines a value of an activity metric based on the activity levels associated with the therapy parameter set.

22. The medical system of claim 21, wherein the processor presents a list of the therapy parameter sets and activity metric values associated with the therapy parameter sets to a user.

23. The medical system of claim 21, wherein the sensors comprise a plurality of orthogonally aligned accelerometers.

24. The medical system of claim 21, wherein the medical device comprises at least one of an implantable neurostimulator and an implantable pump.

25. The medical system of claim 21, wherein the medical device comprises at least one of a trial neurostimulator and a trial pump.

26. The medical system of claim 21, wherein the medical device includes the processor.

27. The medical system of claim 21, further comprising a computing device that includes the processor.

28. A computer-readable medium comprising instructions that cause a programmable processor to:
- monitor a plurality of signals, each of the signals generated by a sensor as a function of at least one of activity or posture of a patient;
- determine whether the patient is in target posture based on at least one of the signals;
- periodically determine an activity level of the patient based on at least one of the signals when the patient is in the target posture;
- associate each of the determined activity levels with a current therapy parameter set; and
- for each of a plurality of therapy parameter sets used by the medical device to deliver therapy to the patient, determine a value of an activity metric based on the activity levels associated with the therapy parameter set.

29. The computer-readable medium of claim 28, further comprising presenting a list of the therapy parameter sets and activity metric values associated with the therapy parameter sets to a user.

* * * * *